US007148267B2

(12) United States Patent
Wachter et al.

(10) Patent No.: US 7,148,267 B2
(45) Date of Patent: Dec. 12, 2006

(54) DYE COMPOSITION FOR THE INDIVIDUAL DYING OF PROSTHESES PLASTICS

(75) Inventors: Wolfgang Wachter, Eschen (LI); Gerhard Zanghellini, Schaan (LI); Volker Rheinberger, Vaduz (LI); Axel Kammann, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 464 days.

(21) Appl. No.: 10/160,828

(22) Filed: May 31, 2002

(65) Prior Publication Data

US 2003/0008936 A1 Jan. 9, 2003

(30) Foreign Application Priority Data

Jun. 1, 2001 (DE) ................................ 101 26 968

(51) Int. Cl.
*A61C 5/04* (2006.01)
*A61K 6/083* (2006.01)
*A61F 2/00* (2006.01)

(52) U.S. Cl. ....................... 523/113; 523/114; 523/120; 106/35; 433/228.1

(58) Field of Classification Search ................ 523/113, 523/114, 120; 106/35
See application file for complete search history.

(56) References Cited

U.S. PATENT DOCUMENTS 3,715,331 A 2/1973 Molnar
4,150,485 A * 4/1979 Lee et al. ................... 523/115
4,521,193 A 6/1985 Cialone
5,125,970 A 6/1992 Klepacki
5,430,074 A 7/1995 Barnes et al.
5,588,834 A 12/1996 Resk et al.
6,224,799 B1 5/2001 Gould
6,281,265 B1 * 8/2001 Montgomery et al. ...... 523/122

FOREIGN PATENT DOCUMENTS

| | | |
|---|---|---|
| DE | 37 19 154 A1 | 6/1987 |
| DE | 696 06 856 T2 | 3/1996 |
| DE | 196 35 667 C2 | 9/1996 |
| EP | 0 836 845 A2 | 4/1998 |
| GB | 640572 | 7/1950 |
| GB | 665293 | 1/1952 |
| WO | WO 01/08638 A1 | 2/2001 |
| WO | WO 01/13814 A1 | 3/2001 |

OTHER PUBLICATIONS

ProBase Hot and ProBase Cold, Product Information Sheet (2001).
Körber et al., “Zahntechnische Herstellung von ästhetisch-funktionellen Brückenkonstruktionen,” DSL pp. 12-14 (1996).

* cited by examiner

*Primary Examiner*—Tae H. Yoon
(74) *Attorney, Agent, or Firm*—Nixon Peabody LLP

(57) ABSTRACT

Kit for the preparation of dental prostheses which contains (i) polymerizable matrix material, (ii) filler and (iii) at least one dye composition in physically separate form.

38 Claims, No Drawings

DYE COMPOSITION FOR THE INDIVIDUAL DYING OF PROSTHESES PLASTICS

The invention relates to dye compositions for the individual dying of plastics for dental prostheses.

It is usual in dentistry to match the colour of restorations individually to the oral-cavity situation of the patient. However, the focus here is primarily on the parts of the restoration which concern the teeth themselves. The colour of gum-coloured parts of prostheses such as for example base plates of complete dentures is matched only crudely, if at all, to the patient in that the dental technician selects a shade which seems suitable to him from a predetermined range of colours.

To prepare base plates of dental prostheses in most cases today two-component systems are used which consist of polymer powder and polymerizable monomer. Powder and monomer are mixed together in a predetermined ratio, poured into a casting mould and cured. The polymer powder is dyed and, depending on the manufacturer, the dental technician has the choice of between 4 to 10 different shades.

U.S. Pat. No. 5,588,834 discloses a system for colour matching of dental restorations which contains colour-modifiers which contain, in addition to acrylic acid monomers and/or polymers, mineral fillers and photoinitiators, dyes such as for example titanium dioxide, iron oxide, chromium compounds or organic dyes. The materials are applied in layers with a brush to plastic caps which then serve the dental technician as a template for the fashioning of the actual restorations, such as crowns and bridges.

Powdered colouring materials for the individual fashioning of dental restorations, which contain metal oxide and, optionally after the addition of a binder, are applied to the restoration with a brush, are known from U.S. Pat. No. 5,125,970.

The Ivoclar Vivadent Targis/Vectris system allows to a limited extent an individual characterization of gum-coloured parts of dental restorations by application of colours in layers.

DE 196 35 667 C2 discloses light-curing opacifiers for covering metal surfaces of dental restorations. The opacifiers contain a cross-linked bead polymerisate into which a coloured pigment is incorporated, and polymerizable polyfunctional monomer.

The known materials for individually colourizing dental restorations are applied in layers and are less suitable for the individual colour-modification of gum-coloured parts of prostheses, as in this case, a complete dying of the material is desired. Materials which allow an individual dying of gum-coloured parts of prostheses are not known to date. As the aesthetic demands made of dental restorations have generally risen, there is a demand for materials which make such a dying possible.

The object of the invention is therefore to provide dental materials which permit the preparation of individually dyed gum-coloured dental prostheses or gum-coloured parts of dental prostheses. By dying is meant a complete, i.e. not merely superficial colouring of the material.

This object is achieved by materials for the preparation of dental prostheses which in addition to polymerizable matrix material and filler contain at least one dye composition. These components are sold as a kit, i.e. in physically separate form, and first mixed together by the user.

According to a preferred version, the kit contains several differently coloured dye compositions, particularly preferably several correction colours and at least one base colour, quite particularly preferably several correction colours and several base colours. The base colour is chosen so that it is as close as possible to the desired shade. An individual matching of the shade is carried out optionally by the addition of the correction colours.

In the case of gum-coloured prostheses or prostheses parts, a complete colouring is sought. The homogenous, streak-free dying of dental materials does however often encounter difficulties, as relatively small amounts of dye must be incorporated uniformly into the material in a reasonable amount of time. An added difficulty is that the mixing devices available to the dental technician and dentist must be used, which are less efficient than industrial mixing apparatuses.

This problem is solved according to the invention by the provision of dye compositions which ensure, even in small quantities, a homogenous distribution in the material and thus a uniform dying, without increasing the mixing outlay compared with conventional two-component systems.

The dye compositions used according to the invention contain a binder and at least one organic or inorganic pigment.

Suitable as polymer-bound pigments are for example the bead polymerisates described in DE 196 35 667 C2 in which a pigment is incorporated into polymer particles. Preferably, the pigment or pigments are however bound only superficially to polymer particles, for example by mixing polymer particles and pigment together intensively. In the process, the pigment or pigments are physically bound to the surface of the carrier polymer particles. The superficial binding of the pigments makes possible a more uniform pigment distribution in the matrix material.

To prepare mixed colours, several differently coloured pigments can be processed simultaneously with one carrier polymer, but preferably the pigments are first bound separately to polymer particles and then the differently pigmented polymer particles are mixed together.

Used as carrier polymers are the polymers common in the dental industry, preferably homo- and copolymers based on (meth)acrylic acid esters, in particular polymethyl(meth)acrylic acid (PMMA) homopolymers and copolymers. Preferably the same materials are used which are also employed in the matrix material, so that cases of cloudiness which are possible when using different materials are avoided and a high transparency and compatibility of the materials is ensured. The carrier polymers are preferably saturated polymers, in particular those with a molecular weight of more than 50,000 g/mol.

The average grain size of the particles of the carrier polymer preferably lies between 20 and 90 μm, it having proved particularly advantageous to use particles with a narrow grain-size distribution. Furthermore, spherical particles are preferred. Particularly preferred are polymer particles with an average grain size of 40 to 50 μm.

Bead polymerisates which can be prepared e.g. in per se known manner by suspension polymerisation in the aqueous phase are particularly suitable as carrier polymers.

The carrier polymers are preferably free from initiator residues, i.e. the residue content of peroxides is less than 0.1 wt.-% in order to avoid an oxidative destruction of the pigments and thereby changes of colour.

Preferred as pigments are heavy-metal-free, i.e. in particular Cd- and Pb-free, pigments. The most common inorganic pigments are those based on the various iron oxides, chromates and molybdates. Mainly used as organic pigments are azo pigments, such as monoazo, disazo, benzimidazolone and isoindolonone pigments as well as polycyclic pigments such as phthalocyanine, thioindigo, flavanthrone, dioxazine and anthanthrone pigments. These substance classes are modified by the use of different substituents with regard to the tint and the colour strength. Preparation, use and properties of the most common organic pigments are described in detail in Herbst/Hunger, "Industrielle Organische Pigmente", VCH-Verlagsgesellschaft, Weinheim, 1987.

Particularly suitable as pigments are ultramarine blue, pigments based on iron oxide, titanium dioxide, cobalt, aluminium, chromium, nickel, zirconium and/or zinc oxides, carbon black and organic coloured pigments. Furthermore, organic pigments, such as for example red diazocondensation pigments e.g. Microlith® rot BR-T (CIBA, Specialities) and yellow benzimidazolone pigments, e.g. PV-Echtgelb H2G 01 (Hoechst) are suitable.

The iron oxide pigments can have a red, yellow, brown or black colour.

Preferred pigments are black iron oxide, brown iron oxide, yellow organic pigment, red organic pigment and titanium dioxide.

The pigment content of the pigmented polymer particles is preferably 1 to 15 wt.-%, in particular 2 to 12 wt.-% relative to the total mass of carrier polymer and pigment, the pigment content depending on the colour intensity of the individual pigments. In the case of white pigments, it is preferably 8 to 12 wt.-%, particularly preferably approx. 10 wt.-%, in all other cases preferably 2 to 4 wt.-%, in particular 2.5 to 3.5 wt.-%. The pigments can be applied to the carrier polymer together with auxiliaries such as e.g. talc.

The dye compositions preferably contain 1 to 80 wt.-%, preferably 2 to 70 wt.-% pigment-containing polymer particles, relative to the total mass of the dye composition.

The dye composition can be in the form of a free-flowing or pasty dispersion or in the form of a pressed article. By dispersions are meant solid-liquid multi-phase systems which contain a solid component insoluble in the dispersion medium.

To prepare dispersions, the pigment-containing polymer particles are reacted with a liquid binder and optionally further auxiliaries such as dispersion auxiliaries and rheological additives, and mixed to a homogenous mass. Depending on the ratio of liquid to solid components, the dispersion is in the form of either a free-flowing or pasty composition.

Preferred as binder for the preparation of dispersions are those substances which swell the carrier polymer. By swelling is meant a surface enlargement of the carrier polymer by the binder, which makes possible a slight loosening of the pigments upon later mixing with the matrix material, which facilitates a homogenous distribution of the pigments in the prostheses material. The storage stability of the dispersions is also improved by the swelling of the polymer particles. Polymerizable monomers are suitable as binders, but not preferred because of their low storage stability.

Particularly suitable binders are phthalates and citrates as well as their mixtures. Particularly preferred is dibutyl phthalate, in particular in combination with carrier polymers based on (meth)acrylic acid esters.

Usual auxiliaries are dispersion auxiliaries and rheological additives. Preferred as rheological additives (thickeners) are highly-disperse silicic acid, layered silicates such as e.g. bentones, hydrogenated castor oils and malonic acid esters, as dispersion auxiliaries talc and wefting agents such as e.g. surfactants.

Preferred dye dispersions have the following composition:

| | |
|---|---|
| Pigment-containing polymer particles: | 8 to 25 wt.-%, preferably 10 to 20 wt.-%, particularly preferably 12 to 18 wt.-%; |
| Binder: | 70 to 92 wt.-%, preferably 78 to 89.5 wt.-%, particularly preferably 80 to 87.5 wt.-%; |
| Auxiliary: | 0 to 5 wt.-%, preferably 0.5 to 2 wt.-%. |

The total pigment content of the dispersions is usually in the range from 0.1 to 10 wt.-%, preferably 0.15 to 6 wt.-%.

To prepare dye compositions in the form of pressed articles, the pigment-containing polymer particles are preferably combined with a solid binder. Hereafter, dye compositions in the form of pressed articles are called tablet-shaped dye compositions or tablets. The choice of binder is of particular importance in this case also. On the one hand, it is intended to guarantee the cohesion of the tablets and prevent a premature decomposition for example during transport, but on the other hand ensure a swift and homogenous distribution of the dye particles upon incorporation of the tablet into the prostheses material.

Preferred binders for the preparation of tablets are materials with melting ranges of 60 to 100° C., preferably 70 to 90° C. and in particular approx. 85° C., such as for example hydrogenated fatty acids, e.g. Thixin®E and Thixin®R (Elementis Specialities, UK), waxy methacrylated polyesters, such as e.g. Uvecoat®9010 (UCB, Belgium) and partly crystalline polyesters. Particularly preferred are materials with a softening point in the range from 35 to 60° C.

By softening point or softening range are meant the temperature or the temperature range at which glasses and amorphous and partly crystalline polymers pass from the vitreous or hard-elastic state into the rubber-elastic state. The softening point lies for most polymers clearly below the temperature at which the polymers pass completely into the liquid state.

The melting point or melting range indicates the temperature at which the liquid and the solid phase of a substance are in thermodynamic equilibrium at 1.013 bar pressure. In the case of amorphous, vitreous substances, there is no specific melting point, as there are crystal lattices here.

The binders preferably have ethylenically unsaturated groups which, upon curing of the prostheses materials, are incorporated into the latter by chemical bonds.

The binder is preferably in particulate form, the particle size preferably being greater than that of the pigmented carrier polymer particles. Preferred are particulate binders with a grain size of 100 to 200 μm and in particular approx. 150 μm. Particles from the polymers preferred as binder have a waxy surface into which the pigmented carrier polymer particles are embedded upon pressing. In this way, a secure cohesion of the tablets is ensured. In addition, when using particulate binders, tablets with a porous structure are obtained which facilitates penetration of the matrix material and thus promotes the dissolution of the tablets and a homogenous distribution of the pigmented carrier polymer particles and of the pigments in the prostheses material.

Moreover, the tablet-shaped dye compositions can also contain inorganic or in particular organic fillers, polymer particles being preferred which are chemically related to the carrier polymers and the matrix material. The fillers are preferably selected such that they do not impair the transparency of the prostheses plastics.

Furthermore, the tablets can contain additives and auxiliaries, for example tabletting auxiliaries. To accelerate the dissolution of the tablets, MBS modifiers such as Paraloid® 736 S (Röhm & Hass) can be added which swell upon contact with the matrix material and in so doing break open the tablets. MBS is the abbreviation according to DIN 7728 Pt 1, 1988 for methacrylate/butadiene/styrene copolymers.

The stearates often used as pressing auxiliaries during the preparation of tablets are unsuitable as additives as they adversely affect the handling of the tablets on the one hand and on the other hand complicate a reproducible and homogenous dying of the prostheses materials. Consequently, the tablet-shaped dye compositions preferably contain no stearates.

The dye compositions, i.e. dispersions and tablets, also preferably contain no initiators for radical polymerization and in particular no peroxides, as the latter can lessen the storage stability of the mixtures by oxidation of organic pigments.

To prepare tablets, pigment-containing carrier polymers, binders and optionally fillers and additives are mixed and then pressed to form tablets. According to the invention, by tablets are meant both cylindrical disks and cubic, square or otherwise shaped bodies. The compression pressure is selected such that the tablet has a strength sufficient for handling. According to a preferred version, the tablet is embossed or provided with indentations on the surface such that an easy division and portioning of the tablets is possible.

After the compression, the tablets can be subjected to an aftertreatment, for example a tempering stage in order to achieve a mechanical hardening of the tablets and improve their handling. The tempering effects a melting of the surface of the polymer used as binder. The tablets preferably have a porous surface in order to make possible a penetration of matrix material. In this way, a swift dissolution of the tablets and a homogenous distribution of the pigmented polymer particles in the prostheses material is ensured. This process can be promoted by a slight heating of the prostheses material.

Preferred tablet-shaped dye compositions have the following composition:

| | |
|---|---|
| Pigment-containing polymer particles: | 1 to 70 wt.-%, preferably 3 to 60 wt.-%, in particular 5 to 50 wt.-%; |
| Binder: | 5 to 80 wt.-%, preferably 10 to 60 wt.-%, in particular 15 to 40 wt.-%; |
| Filler: | 20 to 80 wt.-%, preferably 30 to 70 wt.-%, in particular 35 to 65 wt.-%; |
| Auxiliary: | 0 to 10 wt.-%, preferably 0 to 5 wt.-%, in particular 0.5 to 2 wt.-%. |

The total pigment content of the tablets normally lies in the range from 0.01 to 10 wt.-%, preferably 0.15 to 6 wt.-%.

The kits according to the invention preferably contain, as polymerizable organic matrix material, monofunctional or polyfunctional (meth)acrylates, which can be used alone or in mixtures. Coming into consideration as matrix material are for example methyl methacrylate, isobutyl methacrylate, cyclohexyl methacrylate, tetraethyleneglycol dimethacrylate, triethyleneglycol dimethacrylate, diethyleneglycol dimethacrylate, ethyleneglycol dimethacrylate, polyethyleneglycol dimethacrylate, butanediol dimethacrylate, hexanediol dimethacrylate, decanediol dimethacrylate, dodecanediol dimethacrylate, bisphenol-A-dimethacrylate, trimethylolpropane trimethacrylate, 2,2-bis-[4-(2-hydroxy-3-methacryloxypropoxy)-phenyl]-propane (bis-GMA) as well as the reaction products from isocyanates, in particular di- and/or triisocyanates and OH-group-containing methacrylates.

Examples of this are the reaction products of 1 mol hexamethylene diisocyanate with 2 mol 2-hydroxyethylene methacrylate, of 1 mol tri-(6-isocyanatohexyl)biuret with 3 mol 2-hydroxyethyl methacrylate and of 1 mol 2,2,4-trimethylhexamethylene diisocyanate with 2 mol 2-hydroxyethyl methacrylate, which are called urethane dimethacrylates. The proportion of these mostly long-chained compounds in the matrix material varies between 10 and 80 wt.-%.

Particularly preferred are mixtures of monofunctional (meth)acrylates and polyfunctional (meth)acrylates such as for example mixtures of methylmethacrylate, ethyleneglycol dimethacrylate and/or butanediol dimethacrylate.

As filler, the kits contain inorganic or preferably organic filler, particularly preferably polymer particles based on the above-named binders, preferably homo- and copolymers based on (meth)acrylic acid esters, polymethyl(meth)acrylic acid-(PMMA) homopolymers and copolymers. The fillers preferably have a particle size of 1 to 200 μm, in particular 5 to 100 μm.

The known, dyed polymer powders can be used as filler. In this case, the kit contains as dye composition at least one, but preferably more different correction colours. Kits which contain uncoloured filler and separate base colours and correction colours are preferred.

Preferred kits contain:

| | |
|---|---|
| Matrix material: | 10 to 80 wt.-%, preferably 20 to 70 wt.-%, in particular 27 to 55 wt.-%; |
| Filler: | 20 to 90 wt.-%, preferably 30 to 80 wt.-%, in particular 45 to 70 wt.-%; |
| Dye composition: | 0.2 to 10 wt.-%, preferably 0.5 to 5 wt.-%, in particular 0.7 to 3 wt.-%; |
| Auxiliary: | 0 to 10 wt.-%, preferably 0 to 5 wt.-%, in particular 0 to 2 wt.-%. |

To prepare prostheses, the polymerizable matrix material, filler and at least one dye composition are mixed together and then poured into a suitable mould. The subsequent curing of the material is carried out by heat, light or, given a suitable choice of initiator system, by mixing activator and initiator (cold-curing system).

The curing of the materials is preferably carried out by hot-curing using benzoyl peroxide as initiator. Furthermore, cold-curing systems can be prepared with the customary initiator and activator systems based on amine and peroxide. Preferred are combinations of benzoyl peroxide with tert.-amines such as dimethyl-p-toluidine, or barbituric acid derivatives and metal ions.

According to a preferred version, the kit for the preparation of dental prostheses contains several dye compositions, particularly preferably several base colours and several correction colours. The compositions of base and correction colours are as described above, differing only in number and quantity of the pigments added.

As a rule base colours contain several differently-coloured pigments which are necessary to achieve a particular colour. To achieve a pink or gum-coloured colouring, preferably 4 to 6 pigments are used. A particularly preferred pink-coloured dye composition contains 5 pigments, namely white pigment, preferably titanium dioxide, black pigment, preferably black iron oxide, brown pigment, preferably brown iron oxide, yellow pigment, preferably PV-Echtgelb H2G 01 (Hoechst) and red pigment, preferably Microlith® rot BR-T (Ciba Specialities). By varying the quantities of the individual pigments, different pink base tones can be achieved.

The correction colours preferably contain only 1 or 2 differently coloured pigments, preferably only 1 pigment. Preferred are correction colours which contain a white, black, red or brown pigment.

Preferably, the individual pigments are bound separately to carrier polymer particles and then the pigmented carrier polymers mixed together. The mixture is then processed to a dispersion or tablet. Alternatively, the pigment-containing polymer particles can also be shaped separately to produce dispersions and only then mixed together.

The kits according to the invention preferably contain 4 to 6 base colours. The pigment content and the portion size of the base colours are preferably such that they are sufficient to dye a predetermined quantity of prostheses material, for example the quantity which is required to prepare a prosthesis. In the case of dispersions, the required dye quantity can be packed portionwise in suitable containers or else in dosage dispensers such as e.g. dosage syringes which allow the controlled removal of a specific quantity. In the case of tablet-shaped colour mixtures, the tablet size is chosen accordingly or the tablet shaped such that a problem-free division corresponding to the desired portion size is possible. In this way, the quantities of base and correction colours which are necessary to achieve the desired shade can be ascertained using a colour key, and a controlled and reproducible variation of the colour is made possible.

To prepare dental prostheses such as for example the base plate of complete dentures, matrix material, filler and one of the base colours can be mixed together and thus a prostheses material with the desired base colour obtained. The colour of the prostheses material can then be individually matched by the addition of correction colours. Preferably, however, the necessary quantities of base and correction colour can be ascertained beforehand and using a colour key simultaneously mixed with matrix material and the filler.

By colour key is meant a scale which has as many as possible of the shade which can be obtained with the respective system of base and correction colours. The colour scale advantageously contains a range of individual colour elements which can be removed separately to determine the colour and e.g. can be held up against the gums of the patient. The kits according to the invention preferably contain a colour key and mixing instructions which give the quantities of base and correction colours necessary to obtain the respective shade.

The kits preferably contain 3 to 10 different correction colours, particularly preferably at least a white, black, red and brown correction colour.

The dye compositions according to the invention can be incorporated into the materials for preparing the dental prosthesis without lengthening the mixing time normal to date.

In addition to the components named, the kit according to the invention can contain further optional components to achieve particular effects, such as for example short fibres or polymer spheres. Short fibres, which preferably consist of acetates, PVC or cellulose, can be used loose or in tablet form and serve to achieve modification effects. By adding polymer spheres, the translucence of the materials can be modified. Preferred are polymer spheres made of cross-linked PMMA with a size of 20 to 200 μm, preferably 30 to 100 μm.

A subject of the invention is also a process for the preparation of dental prostheses which is characterized in that (i) a pigment is bound superficially to polymer particles, preferably applied superficially to the particles,
(ii) the pigment-coated polymer particles are combined with a binder and shaped to produce a free-flowing or pasty dispersion or a tablet;
(iii) the dispersion and/or one or more tablets and/or parts of tablets are mixed with a polymerizable matrix material and filler;
(iv) the mixture is shaped to produce a dental restoration or a part thereof and
(v) subsequently cured.

According to a variant of the process, in stage (iii) the polymerizable matrix material and the filler are first mixed with a first dye composition and the shade of the mixture then matched by the addition of one or more further dye compositions to a desired shade. Preferably, however, the necessary quantities of base and correction colours are determined before the mixing as described above and mixed simultaneously with the matrix material and the filler.

To prepare dental prostheses, as a rule, an impression is taken of the patient position (functional mould) and then a master model (plaster model) is produced. The prostheses base is formed with wax on the model and its fit tested on the patient (functional check). The wax model is then set in plastered in a vessel, the wax melted out, the remaining cavity filled with the prostheses material and the material then cured.

By prostheses or dental prostheses are meant in particular base frameworks for dental restorations onto which teeth are fitted, as well as protective prostheses, for example for sport.

EXAMPLES

Example 1

Preparation of Colour Concentrates 88 wt.-% of a bead polymerisate based on methylmethacrylate (Plexidon® M 527, Röhm, average grain size approx. 50 μm) were introduced first in an intensive powder mixer and mixed intensively with 10 wt.-% $TiO_2$ and 2 wt.-% talc. After 10 minutes mixing time, the titanium dioxide and the talc had distributed themselves uniformly on the polymerisate (colour concentrate K1).

To prepare other base colour concentrates, 3 wt.-% black iron oxide (K2), 3 wt.-% brown iron oxide (K3), 3 wt.-% PV-Echtgelb H2G 01 (K4; yellow benzimidazolone pigment) and 2.5 wt.-% of the red pigment Microlith® BR-T (K5; red diazo condensation pigment) were each mixed separately with 97 wt.-% or 97.5 wt.-% bead polymerisate analogously to the method described above.

Example 2

Preparation of Colour Dispersions (Correction Colours)

To prepare a colour dispersion, 84.5 dibutyl phthalate were heated to 60° C. and 15 g of the colour concentrate K1 from example 1 and 0.5 g bentone added and stirred. This mixture was left to stand at 60° C. for 12 hours in order to swell the bead polymerisate. The mixture was then intensively stirred for 15 minutes and cooled to room temperature. The dispersion (D1) thus obtained was ready to use and was able to be packed immediately into dosage syringes or similarly suitable containers.

The correction colours D2 to D5 were prepared analogously based on the colour concentrates K2 to K5.

Example 3

Preparation of a Dispersion (Pink Base Colour)

To prepare a pink-coloured dispersion, the dispersions D1 to D5 were mixed together in the quantities given hereafter by simple stirring:

| | | |
|---|---|---|
| D1 | (white) | 35.7 wt.-% |
| D2 | (black) | 6.1 wt.-% |
| D3 | (brown) | 41.4 wt.-% |
| D4 | (yellow) | 1.1 wt.-% |
| D5 | (red) | 15.7 wt.-% |

The mixture thus obtained was able to be poured into dosing syringes or similar containers and was ready to use.

Example 4

Dying of an Uncoloured Prostheses Plastic Material

To prepare a dyed prostheses plastic, 69 wt.-% PMMA filler and 29 wt.-% matrix material based on methyl methacrylate (monomer) and butanediol dimethacrylate (cross-linker) (Probase® Hot Clear, Ivoclar Vivadent AG) were dyed in a suitable container with 2 wt.-% of the pink-coloured dispersion according to example 3 by simply stirring-in with a spatula and shaped to produce a test article. This was cured by heating to 100° C. within 20 minutes. The testpiece thus prepared had a homogenous pigment distribution and was completely smear-free.

Example 5

Preparation of Tablet-Shaped Dye Compositions (Black Correction Colour)

To prepare tablets of the black correction colour, 65 wt.-% bead polymerisate based on methyl methacrylate (Plexidon® M 527, Röhm, average grain size approx. 50 µm) as filler were mixed with 30 wt.-% polyester (Uvecoat® 9010, UCB, grain size <160 µm, softening range 70 to 90° C.) and 5 wt.-% of the colour concentrate K2 from example 1 and compressed at a pressure of 80 bar to produce tablets with a mass of 0.35 g each. The tablets were then solidified by brief tempering (15 minutes at 100° C.). The press ram was shaped such that the tablets had fracture notches on one side so that they were able to be easily broken into four sections for portioning.

Example 6

Preparation of Pink-Coloured Colour Tablets (Pink Base Colour)

To prepare pink-coloured colour tablets, the components listed hereafter were placed in the specified quantities in a powder mixer and mixed intensively for 10 minutes at room temperature.

| | |
|---|---|
| K1 (white) | 17.5 wt.-% |
| K2 (black) | 3.0 wt.-% |
| K3 (brown) | 20.4 wt.-% |
| K4 (yellow) | 0.5 wt.-% |
| K5 (red) | 8.0 wt.-% |
| Polyester[1)] | 14.3 wt.-% |
| Bead polymerisate[2)] | 36.3 wt.-% |

[1)]UVECOAT ® 9010, UCB, grain size < 160 µm, melting range 70 to 90° C.
[2)]Plexidon ® MW 527, Röhm, average grain size 50 µm 0.35 g in each case of this mixture were compressed in a customary tablet press to produce colour tablets. The pressings from the tablet press were designed such that the tablets had fracture notches on one side so that the tablet was able to be divided into four sections for defined setting of the shades.

Example 7

Dying of Prostheses Plastic

To prepare a dyed prostheses plastic, 24.5 g PMMA filler and 25.1 g matrix material (SR-Ivocap® Clear, Ivoclar Vivadent AG), 1 tablet of the base colour pink according to example 6 and ¼ tablet of the correction colour black according to example 5 were mixed for 5 minutes at room temperature in the mixing capsule of a vibrator mixer (Cap-Vibrator®, Ivoclar Vivadent AG) and a testpiece prepared and cured analogously to example 4. The testpiece had a homogenous pigment distribution and was completely smear-free.

The invention claimed is:

1. Kit for the preparation of dental prostheses which contains (i) polymerizable matrix material, (ii) filler and (iii) at least one dye composition which contains polymer particles and at least one colour pigment which is bound to the polymer particles, in physically separate form.

2. Kit according to claim 1, characterized in that the colour pigment or pigments are applied superficially to the polymer particles.

3. Kit according to claim 1, characterized in that the dye composition contains a bead polymerisate as polymer particles.

4. Kit according to claim 1, characterized in that the dye composition contains polymer particles based on (meth) acrylic acid esters.

5. Kit according to claim 1, characterized in that the polymer particles have an average grain size of 20 to 90 µn.

6. Kit according to claim 5, characterized in that the polymer particles have an average grain size of 40 to 50 µm.

7. Kit according to claim 1, characterized in that the colour pigment is ultramarine blue, iron oxide, titanium dioxide, a coloured pigment based on cobalt, aluminium, chromium, nickel, zirconium and/or zinc oxide, carbon black and/or an organic coloured pigment.

8. Kit according to claim 1, characterized in that the pigment-containing polymer particles contain 2 to 15 wt.-% coloured pigment(s) relative to the total mass of polymer particles and colour pigments.

9. Kit according to claim 1, characterized in that the dye composition further comprises a liquid binder.

10. Kit according to claim 9, characterized in that the binder is selected such that it swells the polymer particles.

11. Kit according to claim 10, characterized in that the binder is dibutyl phthalate.

12. Kit according to claim 1, characterized in that the dye composition is present in the form of a free-flowing or pasty dispersion.

13. Kit according to claim 1. characterized in that the dye composition further comprises a solid binder having a melting point of from 600° C. to 1 000° C.

14. Kit according to claim 9, characterized in that the binder contains ethylenically unsaturated groups.

15. Kit according to claim 13, characterized in that the binder is a partly crystalline polyester.

16. Kit according to claim 13, characterized in that the binder is in particulate form.

17. Kit according to claim 16, characterized in that the binder has a particle size of 100 to 200 μm.

18. Kit according to claim 13, characterized in that the dye composition also contains filler.

19. Kit according to claim 18, characterized in that the dye composition contains as filler polymer particles based on (meth)acrylic acid esters.

20. Kit according to claim 13, characterized in that the dye composition is shaped to produce a tablet.

21. Kit according to claim 1, characterized in that the dye composition contains 1 to 80 wt.-% pigment-containing polymer particles relative to the total mass of the dye composition.

22. Kit according to claim 1, characterized in that it contains several dye compositions in the form of tablets and/or dispersions which can each contain several colour pigments.

23. Kit according to claim 1, characterized in that it contains a colour key and mixing instructions.

24. Kit according to claim 9, characterized in that the colour pigment or pigments are applied superficially to the polymer particles.

25. Kit according to claim 9, characterized in that the dye composition contains a bead polymerisate as polymer particles.

26. Kit according to claim 9, characterized in that the dye composition contains polymer particles based on (meth) acrylic acid esters.

27. Kit according to claim 9, characterized in that the polymer particles have an average grain size of 20 to 90 μm.

28. Kit according to claim 27, characterized in that the polymer particles have an average grain size of 40 to 50 μm.

29. Kit according to claim 9, characterized in that the colour pigment is ultramarine blue, iron oxide, titanium dioxide, a coloured pigment based on cobalt, aluminium, chromium, nickel, zirconium and/or zinc oxide, carbon black and/or an organic coloured pigment.

30. Kit according to claim 9, characterized in that the pigment-containing polymer particles contain 2 to 15 wt.-% coloured pigment(s) relative to the total mass of polymer particles and colour pigments.

31. Kit according to claim 13 characterized in that the binder contains ethylenically unsaturated groups.

32. Kit according to claim 13, characterized in that the colour pigment or pigments are applied superficially to the polymer particles.

33. Kit according to claim 13, characterized in that the dye composition contains a bead polymerisate as polymer particles.

34. Kit according to claim 13, characterized in that the dye composition contains polymer particles based on (meth) acrylic acid esters.

35. Kit according to claim 13, characterized in that the polymer particles have an average grain size of 20 to 90 μm.

36. Kit according to claim 35, characterized in that the polymer particles have an average grain size of 40 to 50 μm.

37. Kit according to claim 13, characterized in that the colour pigment is ultramarine blue, iron oxide, titanium dioxide, a coloured pigment based on cobalt, aluminium, chromium, nickel, zirconium and/or zinc oxide, carbon black and/or an organic coloured pigment.

38. Kit according to claim 13, characterized in that the pigment-containing polymer particles contain 2 to 15 wt.-% coloured pigment(s) relative to the total mass of polymer particles and colour pigments.

* * * * *